United States Patent [19]

Murphy et al.

[11] Patent Number: 4,468,136
[45] Date of Patent: Aug. 28, 1984

[54] OPTICAL BEAM DEFLECTION THERMAL IMAGING

[75] Inventors: John C. Murphy, Columbia; Leonard C. Aamodt, Silver Spring, both of Md.

[73] Assignee: The Johns Hopkins University, Baltimore, Md.

[21] Appl. No.: 348,369

[22] Filed: Feb. 12, 1982

[51] Int. Cl.³ .................. G01N 21/00; G01N 25/00
[52] U.S. Cl. ..................... 374/45; 250/334; 374/17; 374/124; 356/128; 356/432
[58] Field of Search ............... 374/112, 5, 123, 124, 374/130, 45, 186; 356/432, 128, 70; 73/579

[56] References Cited

U.S. PATENT DOCUMENTS

| | | | |
|---|---|---|---|
| 3,222,917 | 12/1965 | Roth | 374/5 |
| 3,427,861 | 2/1969 | Maley | 374/124 X |
| 3,433,052 | 3/1969 | Maley | 374/124 X |
| 3,451,254 | 6/1969 | Maley | 374/5 |
| 3,482,448 | 12/1969 | Gaffard | 374/112 |
| 3,504,524 | 4/1970 | Maley | 374/5 |
| 3,681,970 | 8/1972 | Wells | 374/5 |
| 3,688,189 | 8/1972 | Lamb | 356/128 X |
| 3,948,345 | 4/1976 | Rosencwaig | 73/579 |
| 4,023,201 | 5/1977 | Faulkner | 374/124 |
| 4,083,223 | 4/1978 | Hashimoto | 374/5 |
| 4,213,699 | 7/1980 | Moore | 356/70 |
| 4,227,369 | 10/1980 | Williams | 374/123 |
| 4,299,494 | 11/1981 | Badoz et al. | 356/432 |
| 4,365,307 | 12/1982 | Tatsuwaki et al. | 374/124 X |

OTHER PUBLICATIONS

Publ. IBM Technical Disclosure Bulletin, vol. 21, No. 10, Mar. 1979, "Trace Analysis in Gases by Laser-Induced Schlieren Technique", Hermann et al., pp. 4208–4209.

*Primary Examiner*—Daniel M. Yasich
*Attorney, Agent, or Firm*—Robert E. Archibald; Howard W. Califano

[57] ABSTRACT

The present invention provides a thermal imaging method to evaluate the surface and subsurface properties of a material and is based on techniques of optical beam deflection thermal imaging. The invention uses a localized excitation source, such as an optical beam, to provide localized heating of the sample surface. A surface thermal gradient is induced on the sample surface as heat flows, in three dimensions, from the area of localized excitation into the test material. The surface temperature gradient causes a thermal refractive lens to be generated in the fluid (gas or liquid) adjacent to the sample surface. An optical probe beam is directed through the thermal lens and is deflected by changes in a refractive index of the thermal lens. Changes in the refractive index are induced by variations of the surface temperature. In this manner, a detailed surface temperature profile can be generated which reveals surface and subsurface properties of the material tested.

46 Claims, 18 Drawing Figures

OPTICAL BEAM DEFLECTION THERMAL IMAGING

STATEMENT OF GOVERNMENT INTEREST

The Government has rights in this invention pursuant to Contract No. N00024-81-C-5301 awarded by the Department of the Navy.

BACKGROUND OF THE INVENTION

1. Field of the Invention

The invention relates generally to a method and apparatus of thermal imaging used to determine surface and subsurface properties and structure of a sample material. More particularly, the invention deals with a method of dynamic thermal imaging called optical beam deflection wherein an optical probe beam scans the sample surface through a thermal lens generated in the fluid (liquid or gas) adjacent to this surface. An excitation beam heats a localized area on the sample surface generating the thermal refractive lens. The vectorial deflection of the optical probe beam is measured as it scans across the thermal lens. This in turn provides information about properties and features found in the surface and subsurface layers of the sample.

2. Description of the Prior Art

It is well known that the surface temperature of a heated object depends upon its thermal and structural properties (and its optical properties when light is used as a heating source). Several methods of thermal imaging have been used to determine the properties of a sample as a function of the surface temperature profile. Several of the more significant methods include radiometric thermal imaging, photoacoustic imaging and piezoelectric photo imaging.

U.S. Pat. No. 3,504,524, issued to D. R. Maley, uses a radiometric method of thermal imaging wherein the surface temperature is detected by observing localized changes in thermal radiation emitted by the sample. The patent teaches the heating of a sample and the use of a radiometer to detect the thermal energy emitted. The radiometer is aimed at one particular area of the sample surface and locates defects by detecting changes in thermal energy levels. However, problems have been experienced with detector sensitivity, dynamic range and signal discrimination.

Another method of thermal imaging is called photoacoustic imaging. For this method the test sample is placed in an enclosed cell which is filled with a gas. The sample is heated and boundary heating between the sample and the gas produces a pressure wave in the cell which is detected using a sensitive microphone. The method has several serious drawbacks: (1) it requires an enclosed cell which limits the size and type of samples that can be used; (2) it can only detect the average temperature over the entire sample surface, and (3) since the heat source is not localized, three-dimensional heat flow is not significant and less information on surface and subsurface features is available.

Another thermal imaging technique uses a piezoelectric detection method wherein a sample is heated locally, generating stress waves in the specimen which are caused by local thermal expansion. A piezoelectric transducer, bonded to the sample or in contact with the sample via some coupling fluid, detects the stress waves. U.S. Pat. No. 3,222,917, issued to W. Roth, discloses an apparatus wherein a thermal pulse is applied to a localized region and thermal effects are detected by a "pickup transducer" some distance from the thermal pulse source. This method also has several disadvantages: (1) contact is required between the testing device and sample; (2) where large samples are tested, acoustic phase delays are present which must be considered; and, (3) the method does not have the advantages of localized detection unless some type of acoustic lens is used in a manner of the "photoacoustic microscope".

Although the prior art methods recognize the usefulness of thermal imaging to determine structural characteristics of a sample, they were mainly concerned with one-dimensional heat flow analysis. The belief in the prior art, as summarized in an article entitled "Scanned Image Microscopy" by D. Fournier and A. C. Boccara, published by Academic Press (1980), was that three-dimensional diffusion effects were insignificant to thermal imaging.

SUMMARY OF THE INVENTION

The present inventors recognized the additional information that a three-dimensional heat flow model would provide and developed a technique which allows for both localized excitation and detection. A modulated excitation beam is directed to the surface of the sample being tested and provides an area of localized heating. Heat flows from the area of localized heating both into the sample and along the sample surface, creating a surface temperature gradient in the area of localized heating. The surface temperature gradient in the fluid (gas or liquid) adjacent to the sample surface produces a thermal refractive lens. The shape of the thermal lens provides information about surface or subsurface inhomogenieties. As symmetrical lens generally indicates the presence of a homogeneous sample whereas a non-symmetrical thermal lens indicates the presence of thermal blooming caused by a surface or subsurface defect or inhomogeniety. An optical probe beam is directed to pass through the thermal lens and will be refracted by the thermal lens. The optical probe beam's vectorial deflection both normal to the sample surface and in the plane of the sample surface is measured by an optical beam detecting means. As the optical probe beam scans across the thermal lens, the vectorial displacement is recorded. Compiling this information will provide knowledge as to the shape of the thermal lens, and therefore will provide information on the surface and subsurface structure and properties. Prior art thermal imaging techniques did not use localized detection and measured the average modulated temperature over a portion of the sample heated. The invented technique measures the average modulated surface temperature along the projection of the probe beam passing through the area of localized heating. By changing the position and direction of the probe beam and by pointing the excitation beam to a plurality of different positions, a detailed temperature profile for the entire sample can be mapped out.

One unique feature of this invention is that the vectorial probe beam deflection can be separated into a normal and transverse component. The transverse component is of particular interest because it enhances the identification of inhomogenieties. When the excitation beam scans a homogeneous sample, the transverse component of the probe deflection will be zero as long as the probe and excitation beams intersect. When a defect or inhomogeniety is present, however, a non-zero transverse deflection is obtained. This defect-induced deflection is superimposed on what otherwise would be a null signal and thus is easily observed. Prior art defect-induced signals are superimposed and masked by a large signal produced by normal absorption in the sample. This feature makes the invented method and apparatus uniquely suited for detecting inhomogenieties in surface and subsurface layers of the material and provides a unique non-destructive testing of materials.

One novel feature of the invented method and apparatus is that non-contact testing can be made under normal environmental conditions without the need of an enclosed cell.

Another novel feature is the use of an excitation beam which provides localized heating. The area of localized heating is small, so that there is a larger surface gradient and temperature heat flow. This feature allows one to study the three-dimensional heat flow thus providing additional information on surface and subsurface inhomogenieties.

Another novel feature is the use of an optical probe beam which provides localized detection. The optical probe beam is directed through the thermal lens generated in the fluid above the sample. The probe beam's deflection is a measure of the average modulated surface temperature along the projection of the probe beam passing through the heated area.

Another novel feature of optical deflection thermal imaging is that it is possible to isolate the transverse deflection of the optical probe beam. This feature is extremely important in the non-destructive testing of materials and provides an enhancement of the defect-induced signal.

BRIEF DESCRIPTION OF THE DRAWINGS

FIG. 10a illustrating the test sample which contained a crack; FIG. 10b showing the transverse deflection component of the optical probe beam; and, FIG. 10c showing the normal deflection of the optical probe beam as it scans across the test sample.

FIG. 12a shows a beam orientation when light is masked by the knife edge; and, FIG. 12b shows a beam orientation when light does not intersect the knife edge.

DETAILED DESCRIPTION OF THE PREFERRED EMBODIMENT

Figure 1:
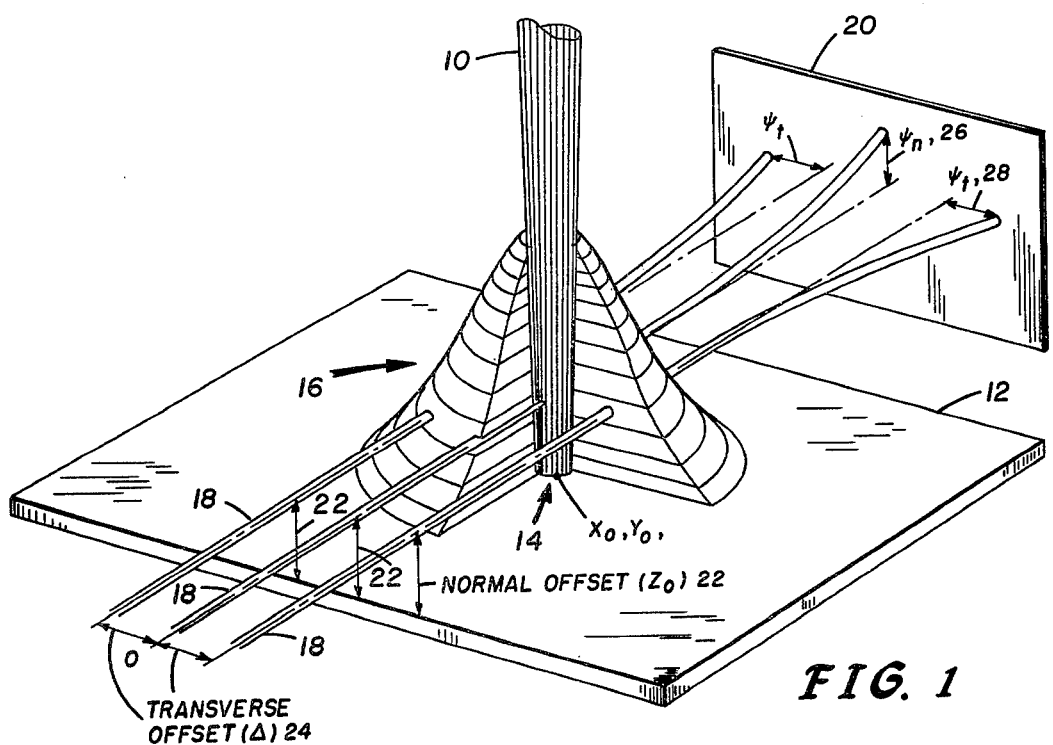
FIG. 1 is an enlarged diagramatic representation of optical beam deflection thermal imaging.

FIG. 1 shows an enlarged diagramatic representation of the proposed optical beam deflection technique being used for the non-destructive testing of the materials. An excitation beam 10 is directed to the surface 12 of the sample being tested and produces heating in a localized area 14 of the sample surface. Heat flows in three dimensions from the area on the surface heated by the excitation beam into and along the surface of sample material and produces a thermal gradient on the sample surface. The surface temperature in the area of localized heating 14 causes a thermal refractive lens 16 to be generated in the fluid above the sample. An optical probe beam 18 is directed through the thermal lens 16 and is refracted by the thermal lens. An optical detecting means 20 measures the vectorial deflection of the optical beam. The optical probe 18 skims along the sample surface at a normal offset 22 ($Z_o$) above the surface, and can be displaced a transverse offset 24 ($\Delta$) on either side of a center position. (A center position occurs when the optical probe beam 18 intersects the excitation beam 10.)

Various methods will be described for scanning the probe beam 18 across the thermal lens 16 and for determining the vectorial displacement of the probe beam 18 which provides detailed data on the shape of the thermal lens 16. The shape of the thermal lens 16 provides information on the three dimensional heat flow into the sample and in particular identifies a localized increase or reduction of the heat flow into or along the sample material. Areas of significant temperature enhancement on the surface causes thermal blooming which produces an asymmetrical thermal lens. Areas of significant temperature enhancement are caused by inhomogenieties, such as: cracks, fatigues or strain in the surface or subsurface layers of the material. The shape of the thermal lens 16 also indicates properties of the test material such as thermal conductivity.

As the optical probe beam 18 passes through the thermal lens 16 it experiences a vectorial deflection which can be represented in terms of a normal 26 and transverse 28 deflection components. The refraction of the probe beam as it passes through the thermal lens can be represented by the following equation:

$$\vec{\psi} = -\int_P dn/ndT \nabla T_g \times d\vec{l} \qquad (1)$$

wherein n is the fluid index of refraction, $T_g$ is the fluid temperature at a particular point generated by the material surface temperature, P is the optical probe beam path (over the sample), and dl is a vectorial notation for an incremental distance along P. Since equation 1 involves a vectorial cross-product, the probe beam deflection can be separated into two orthogonal components ($\psi_n$ and $\psi_t$), both normal to the incident optical probe beam. The normal component ($\psi_n$) represents a deflection normal to the sample surface, while the transverse component ($\psi_t$) represents a deflection in the plane parallel to the sample surface. As the transverse offset ($\Delta$) of the optical probe beam is varied, the transverse and normal components of deflection, as measured by the optical detection means 20, will vary. Explicit expressions for these two deflection components, $\psi_n$ and $\psi_t$, are described by the following equations:

$$\psi_n = 2 T_o^{-1} \int_o \overline{T}_s (\lambda) b_g \exp(-b_g Z_o) \cos(\lambda y) d\lambda \qquad (2)$$

$$\psi_t = 2 T_o^{-1} \int_o \overline{T}_s (\lambda) \lambda \exp(-b_g Z_o) \sin(\lambda y) d\lambda \qquad (3)$$

wherein $T_o^{-1} = dn/ndT$, $Z_o$ is the probe beam normal offset, y is the probe beam transverse offset, $\overline{T}_s$ is the Fourier transform of the sample surface temperature, and $b_g = \sqrt{\lambda^2 - 2j/\delta_g^2}$, and $\delta_g$ is the fluid thermal diffusion length.

Figure 2:
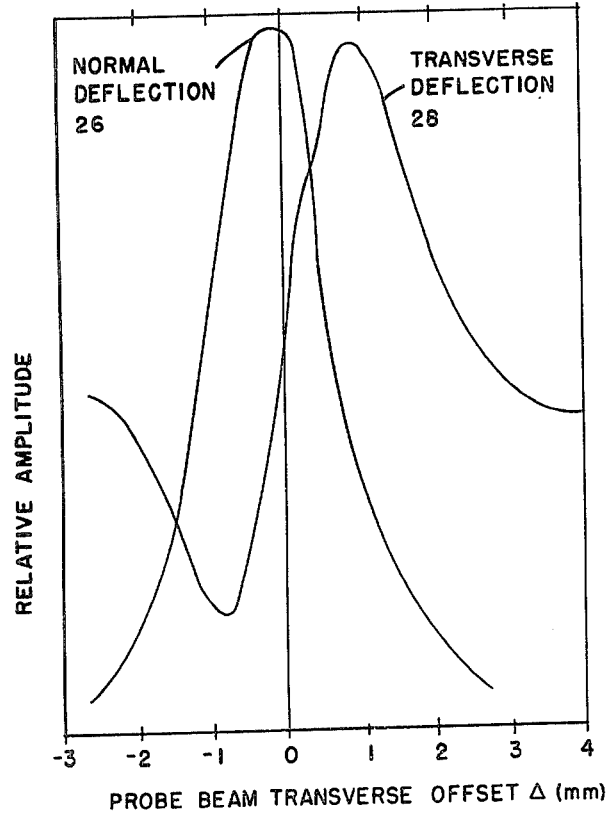
FIG. 2 is a graph showing measurements of transverse and normal deflection components of the optical probe beam.

FIG. 2 shows experimental measurements of the transverse and normal components of the beam deflection, taken for a homogeneous thin silicon wafer, which confirm the theoretical equations indicated above. As indicated in FIG. 2, the normal deflection component 26 ($\psi_n$) has a symmetric profile which is essentially gaussian in shape when a gaussian excitation beam is used to heat a homogeneous sample. By contrast, the transverse deflection component 28 ($\psi_t$) has an antisymmetric profile which is unique to this spatially localized detection method and helps enhance the identification of inhomogenieties. When the excitation beam scans a locally homogeneous sample, with thermal properties spatially invariant on the scale of a thermal diffusion length, the transverse probe beam deflection will remain zero as long as the probe and excitation beams intersect, i.e., ($\Delta=0$). When a defect is present, however, the homogeneous condition is broken and a non-zero transverse deflection is obtained. This defect-induced deflection is superimposed on what otherwise would be a null signal and thus is easily observed. A defect-induced signal is also obtained for the normal deflection component but it is superimposed on a large signal produced by normal optical absorption in the sample. Only in the invented optical beam deflection technique is a null signal obtained in the absence of defects.

Figure 3A:
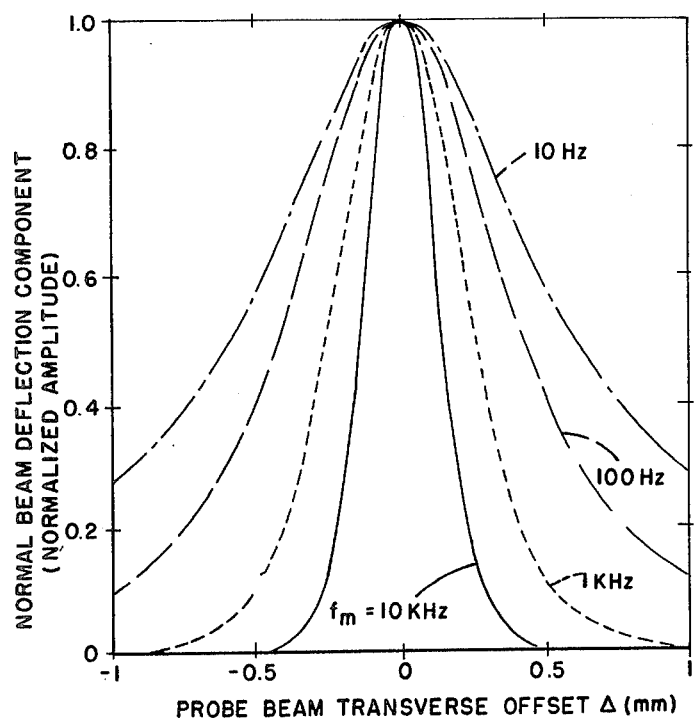
FIG. 3a is a graph showing the normal deflection component of the optical beam as a function of the probe beam transverse offset for various excitation beam modulation frequencies.
Figure 3B:
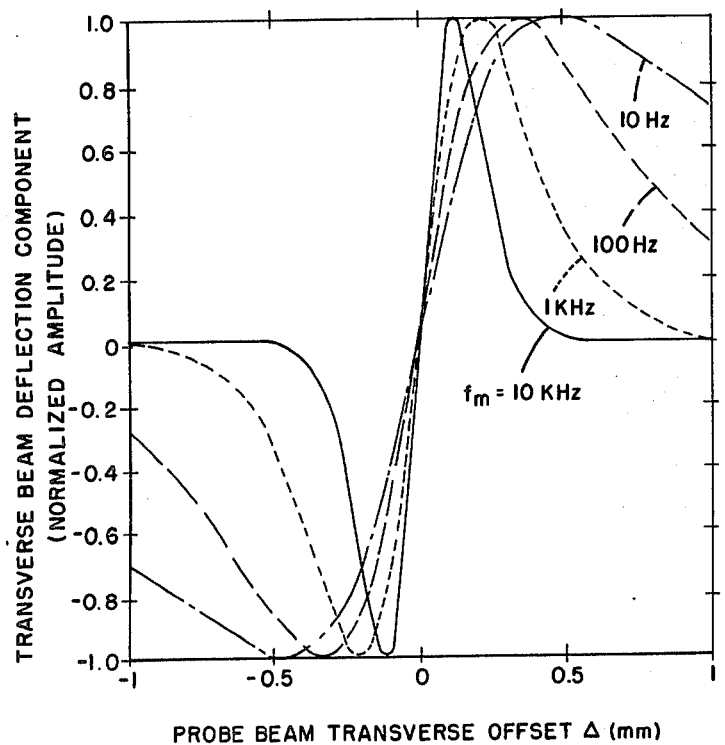
FIG. 3b is a graph showing the transverse deflection component of the optical probe beam as a function of the probe beam transverse offset for various excitation beam modulation frequencies.

FIG. 1 shows the thermal lens 16 generated at a particular instant in time. To enhance detection, the excitation beam is modulated. The modulated excitation beam produces a dynamic temperature change in the area of localized heating 14 and causes the thermal lens 16 to alternate or pulsate in size. The transverse and normal deflection components of the optical probe beam will also vary in amplitude and phase as the refractive properties of the thermal lens change. FIG. 3a shows variations in the normal deflection component, and FIG. 3b shows the deflection of the transverse deflection component, as the modulation frequency ($f_m$) is varied. (NOTE: The measurements shown in FIGS. 2 and 3 represent the normal and transverse component deflection amplitude with reference to the excitation beam modulation). The beam can be modulated by many available techniques. The beam can be amplitude, phase, frequency, or spatially modulated so as to create a dynamic temperature change on the sample surface. The frequency of modulation is adjusted to vary the depth of penetration into the sample. If the frequency of modulation is decreased, the thermal diffusion length in the sample is increased and the depth of penetration into the sample is increased. If the surface or layer close to the surface is to be analyzed, the frequency is increased, thereby decreasing the thermal diffusion length into the sample. FIG. 3 shows the transverse and normal deflection pattern of the optical beam as a function of the excitation beam modulation frequency ($f_m$).

The excitation beam 10 is generally a beam of electromagnetic radiation which can be coherent or incoherent, focussed or unfocussed. Electromagnetic energy can vary in frequency from the microwave range having a frequency of 10 MHz to the ultraviolet light frequency of $10^{15}$ Hz. The excitation beam 10 can be an electron or particle beam. The excitation beam 10, shown in FIG. 2, is projected normal to the surface of the sample. However, this is not a requirement and any incident angle of the excitation beam 10 would be satisfactory to heat a localized area on the sample surface. The excitation beam used to test the samples shown in FIGS. 2 and 3 was produced by a laser source having a circular beam of light with a gaussian distribution.

The optical probing beam 18 may be of coherent or incoherent light and is of a diameter much smaller than the thermal lens. Applicants have used an optical probe beam having an approximate 1 mm beam width.

A thermal lens 16 is produced in the fluid layer adjacent to the surface of the sample. The fluid may be a liquid or a gas and if it is a gas it may be at atmospheric pressure or it may be at a reduced or increased pressure level. It will be noted that one of the novel features of optical beam deflection thermal imaging is that no enclosed cell is needed consequently, relatively large samples may be used and may be tested in their natural environment.

Figure 4:
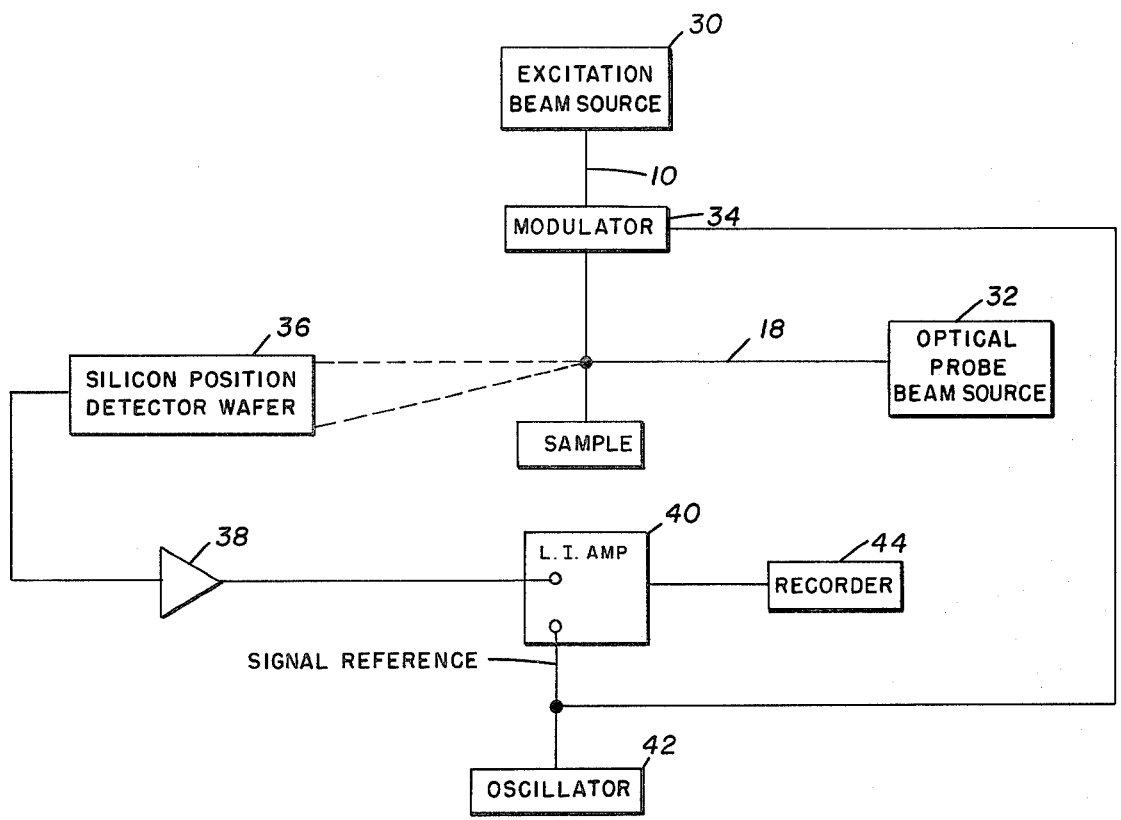
FIG. 4 is a block diagram of a typical apparatus used in the proposed optical beam deflection thermal imaging.

FIG. 4 shows, in block diagrammatic form, a typical optical beam deflection apparatus. The apparatus generally consists of: an excitation beam source 30; an optical probe beam source 32; a modulator 34 which can either amplitude or pulse modulate the excitation beam 10; a silicon position detection wafer 36 which has an output voltage dependent on the location the optical probe beam strikes the wafer surface; an amplifier 38; a lock-in amplifier 40 which receives as input the amplified signal from amplifier 38; oscillator 42, which generates a reference signal for the lock-in amplifier and modulator 34; and, recorder 44 which records the output signal from the lock-in amplifier 40. In operation, the silicon position detector wafer 36 generates an output voltage as a function of the beam displacement from a center position. Voltage from the silicon position detector wafer 36 is amplified by amplifier 38 and processed by the lock-in amplifier 40. The lock-in amplifier provides frequency sensitive detection and is synchronized by a reference signal generated in oscillator 42. The apparatus of FIG.

4 can be set so that the amplitude of the transverse and normal components of the optical probe beam deflection can be measured at a particular phase during the excitation beam modulation cycle.

Figure 5:
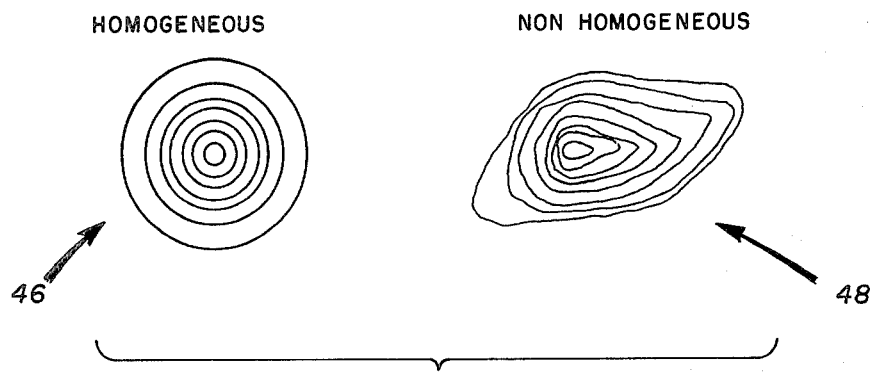
FIG. 5 is a pair of contour graphs showing the surface temperature gradient of sample materials with and without inhomogenieties.

FIG. 5 shows a topographical representation of the surface temperature distribution for a homogeneous and a non-homogeneous sample material. As has been mentioned previously, as the optical probe beam passes through the thermal lens it is deflected and its deflection has normal and transverse components. The optical detection means 20 (illustrated in FIG. 4) measures the extent of normal or transverse deflection. Allowing the probe beam to take several different paths through the thermal lens, and measuring its deflection vector, enables one to know the overall shape of the thermal lens. If the material being tested is homogeneous, a thermal lens generated above the area of localized heating will have a symmetrical shape, as shown in graph 46 of FIG. 5. If however, the material has surface or subsurface inhomogenieties, cracks, or areas of fatigue, the temperature distribution on the surface of the material will not be symmetrical. The resulting surface temperature distribution will have areas of thermal enhancement and will appear non-symmetrical as shown in graph 48 of FIG. 5. A non-symmetrical surface temperature distribution will induce a non-symmetrical thermal lens in the fluid above the sample surface.

Figure 6:
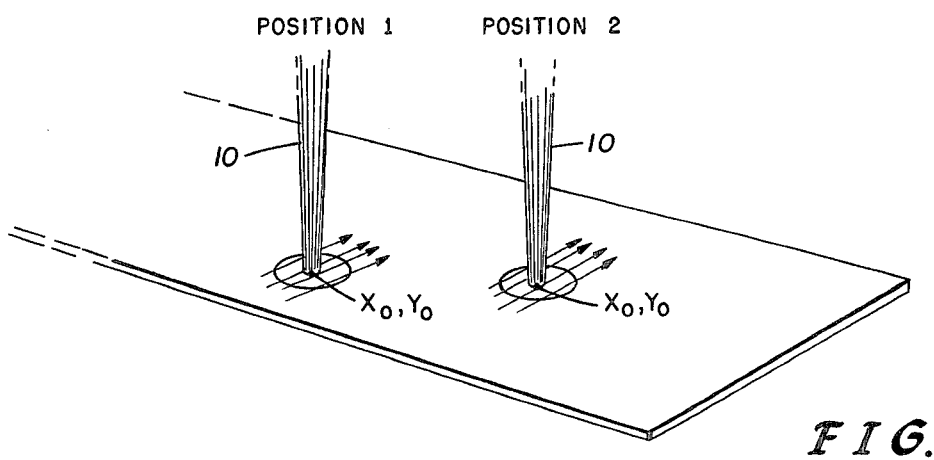
FIG. 6 is an enlarged diagrammatic representation of a transverse scanning scheme.
Figure 7:
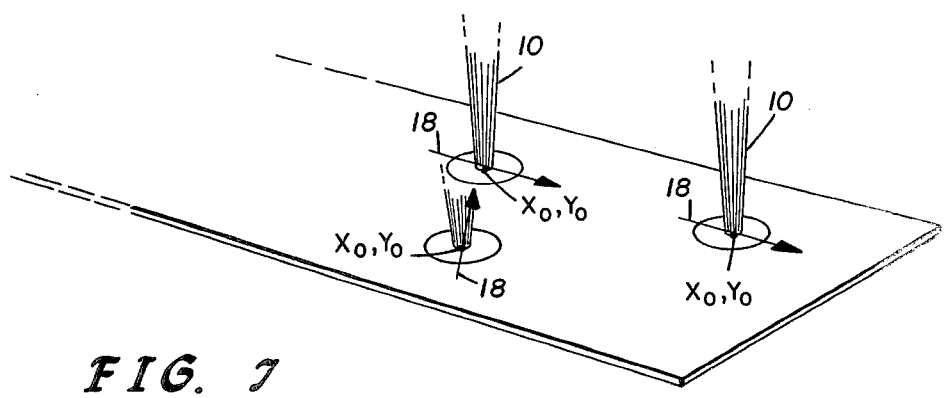
FIG. 7 is an enlarged diagrammatic representation of the standard scanning scheme in accordance with the invention wherein the optical probe beam intersects the excitation beam.
Figure 8:
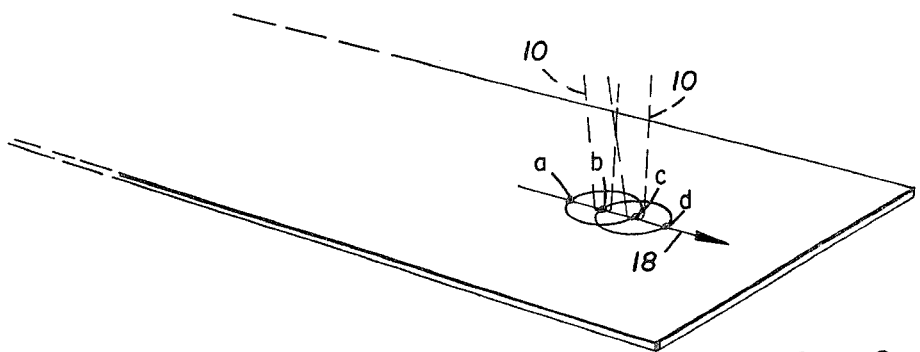
FIG. 8 is an enlarged diagrammatic representation of an alternative scanning method in accordance with the invention wherein the optical probe beam is held stationary and the excitation beam is pointed to intersect with the probe beam and is moved along a portion of the probe beam.

FIGS. 6, 7 and 8 shows several scanning methods which can be used to determine the shape of the thermal lens. FIG. 6 illustrates a transverse scanning scheme wherein the optical probe beam 18 scans across the thermal lens 16 at a normal offset ($Z_o$) from the sample surface and the vectorial deflection of the optical probe beam is measured for various values of the transverse displacement ($\Delta$). In this manner, the shape of the thermal lens above the area of localized heating centered at coordinates ($X_o$, $Y_o$) is obtained. To determine the surface or subsurface characteristics of a large sample, the excitation beam 10 is pointed to a plurality of positions on the sample surface ($X_o$, $Y_o$), the probe beam is caused to transversely scan across the thermal lens generated from each excitation beam position, and the optical detecting means measures the optical probe beam vectorial deflection. The vectorial deflection for excitation beam positions ($X_o$, $Y_o$) and transverse displacements ($\Delta$) are recorded.

FIG. 7 illustrates the standard scanning scheme wherein the optical probe beam 18 intersects the excitation beam 10 (transverse displacement ($\Delta$) is zero). The normal and transverse deflections of the optical probe beam are then measured by the optical detecting means 20. In this configuration the transverse deflection component is of extreme value because it will have a zero value if the thermal lens is symmetric and it will have a positive or negative value if the thermal lens is of a non-symmetric shape. As mentioned previously, the non-symmetric shape is caused by surface or subsurface inhomegenieties. To determine the surface and subsurface characteristics (e.g., inhomogenieties, such as cracks or subsurface fatigue) the excitation beam is pointed to a plurality of different positions ($X_o$, $Y_o$) on the sample surface and the optical probe beam 18 is projected to intersect with the excitation beam 10 for each new position of the excitation beam 10.

FIG. 8 illustrates an alternative method of standard scanning wherein the optical probe beam 18 is held stationary and the excitation beam 10 is pointed to intersect with the probe beam and is moved along a portion of the probe beam. The normal and transverse deflection of the optical probe beam are measured at various positions of the excitation beam ($X_o$, $Y_o$).

Edge Enhancement in Optical Beam Deflection Techniques

One specific application of the optical beam deflection apparatus and method is in the area of non-destructive testing for cracks or areas of fatigue. For this particular application, the probe beam intersects the excitation beam (transverse displacement $\Delta=0$), and the transverse and normal deflection of the optical probe beam is measured at a particular phase of the excitation beam modulation cycle. The excitation beam is directed to a plurality of positions on a sample surface ($X_o$, $Y_o$) and the deflection of the intersecting optical probe beam is measured.

Figure 9:
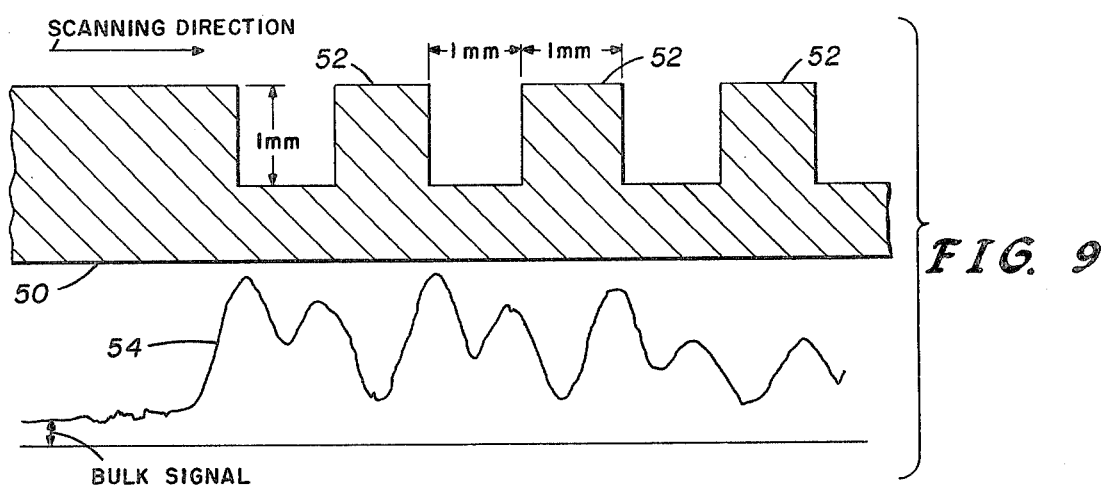
FIG. 9 is an enlarged view of a sample that was tested in accordance with the invention and the resulting normal optical beam deflection.

The graph in FIG. 9 shows an increase in the normal deflection component of the optical probe beam near thermal boundaries. A test model 50 (shown in FIG. 9) was made from an aluminum block containing a series of 1 mm deep and 1 mm wide slots, each slot being separated by a "mesa" 52 of 1 mm. A focused argon laser beam approximately 25 microns in diameter and modulated a 11 Hz was used to provide localized heating on the slotted side of the test sample. A helium-neon laser produced a probe beam, which was oriented such that the probe beam and excitation beam intersect. The sample is scanned by the excitation beam and the probe beam is directed to intersect each new excitation beam position. The normal component of the optical beam deflection is detected by a silicon position detection wafer which provides an output voltage which increases in amplitude as the optical probe beam is deflected away from the sample surface. As the sample is scanned, the signal increases significantly when the first slot edge is reached (see the graph 54 in FIG. 7), and as the scan continues across the various slots, the normal beam deflection signal is again enhanced at each slot edge. As the excitation beam moves away from the edge and towards the mesa, the signal decreases.

The results obtained from the test model using a localized excitation source can be summarized as follows: For wide slots, or in the bulk material, the heat developed by or near the sample surface quickly diffuses into the sample bulk, leaving a relatively small sample surface temperature. This heat diffusion is both normal (into the sample) and transverse (parallel to the plane of the sample). As the slots become more narrow, the transverse heat flow is interrupted. Consequently more heat must be channeled vertically, producing a delay in heat dissipation and a corresponding rise in surface temperature. This effect is purely three-dimensional and is not included in conventional photo acoustical system theory, which is one-dimensional and considers only normal heat flow.

Figure 10A:
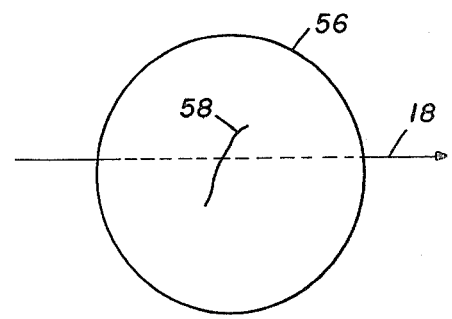
FIGS. 10a–c illustrate the application of optical beam deflection to detect a crack on a wafer test sample.
Figure 10B:
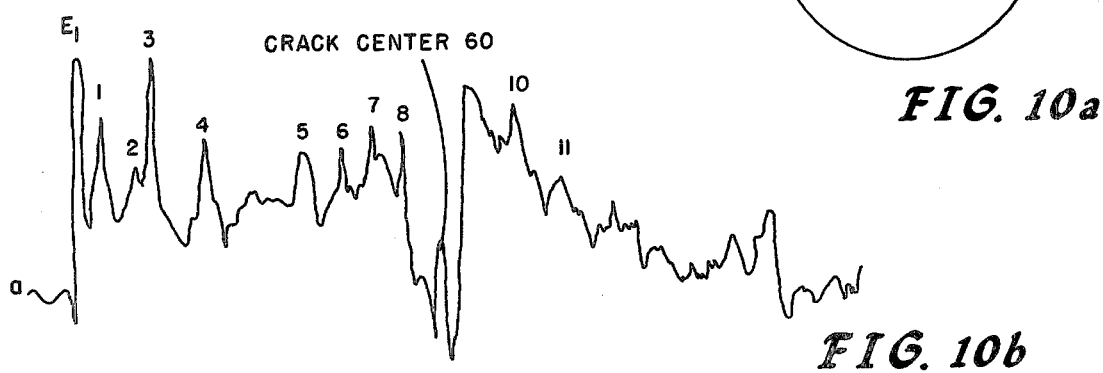
Figure 10C:
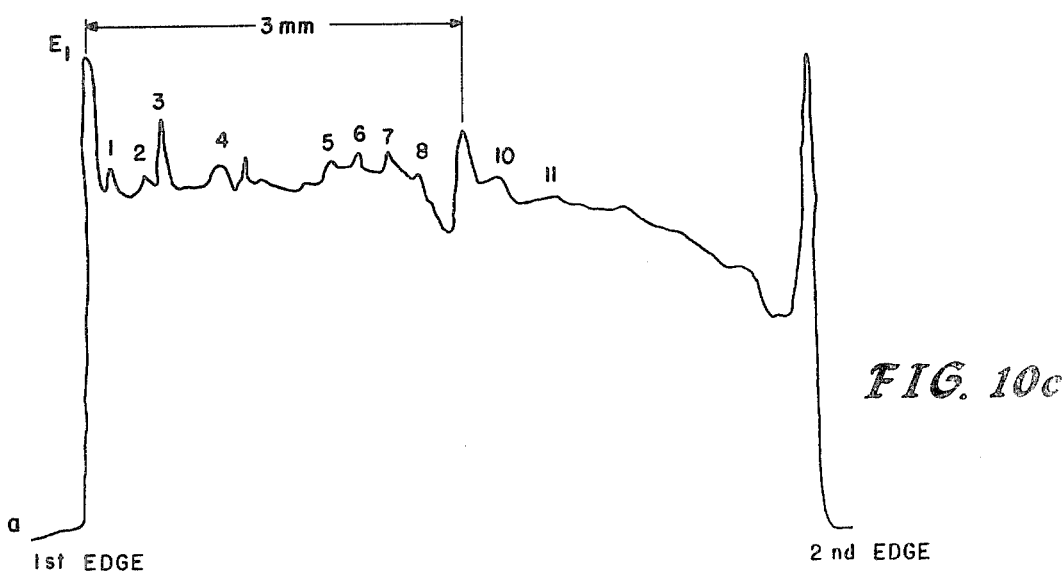

FIG. 10 shows the application of the optical beam deflection method and apparatus to a more practical crack detection problem and illustrates the usefulness of measuring the transfers deflection component of the optical probe beam The test sample 56 was made from a $TiO_2/VO_2$ ceramic wafer containing a fine crack 58 approximately $25\mu$ in width and extending across the face of the sample. A silicon position detection wafer is again used to measure normal and transverse optical probe beam deflection components by producing an output voltage which increases as the extent of deflection inceases. Note that, since the optical probe beam and excitation beams intersect, the transverse deflection component is zero in absence of non-symmetries in the thermal lens and therefore insensitive to spatial changes in the sample's absorptivity and reflectivity. The graph in FIG. 10b shows the intensity of the transverse deflection as the sample is scanned and the graph in FIG. 10c shows the normal deflection as the sample is scanned. The normal deflection scan shows edge effects similar to those observed in FIG. 9. The transverse scan (see FIG. 10b) shows the somewhat enhanced edge effect signal 60 as the excitation beam scans across the crack on the wafer surface. Both the normal and the transverse components show the presence of the crack as well as other features which could be visually correlated with defects using an optical microscope. Corresponding features in the transverse and normal graphs of FIG. 10b and 10c, respectively, are identified by number and include, among other factors, surface relief changes and inclusions of foreign particles. However, for the transverse deflection component the signature of the crack signal 60 is clearly recognizable.

Both FIGS. 9 and 10 shows specific cases of thermal imaging using the optical beam deflection method and apparatus. In the application shown in FIG. 10 a three-dimensional heat flow into and along the surface of the test material causes an enhanced transverse deflection of the optical probe beam. These special applications of optical beam deflection are unique in that non-destructive testing can be accomplished without requiring physical contact with the material being tested and without the requirement of enclosing the sample in an acoustically isolated cell. This allows the optical beam deflection method and apparatus to inspect large specimens under conventional laboratory environmental conditions.

It is obvious however that the optical beam deflection method and apparatus can be generally used to determine the nature of these dimensional heat flow into the sample. Optical beam deflection measurements are used to map out the shape of the thermal lens created in the fluid above the sample. The shape of thermal lens is dependent upon the sample surface temperature gradient which is dependent on the rate of heat flow into and along the sample surface. The optical beam deflection method and apparatus, utilizing localized heating and localized detection, permits measurements to be made of the optical and thermal structure in heterogeneous materials and in fabricated structures (e.g., determining the structural order in integrated circuits). By studying the frequency dependence of the optical beam deflection on the modulation phase of the excitation beam, changes in the optical and thermal properties with depths below the surface can be inferred. The optical beam detection method and apparatus can: characterize laser surface hardening of metal and analyze heat affected zones; characterized deformation regions associated with indenter studies of metals; and, localize and characterize cracks, areas of fatigue, and regions of internal strain in metal and ceramics. Many other useful applications of the optical beam detection method and apparatus are apparent to one familiar with the non-destructive testing of material.

Alternative Embodiments

Figure 11:
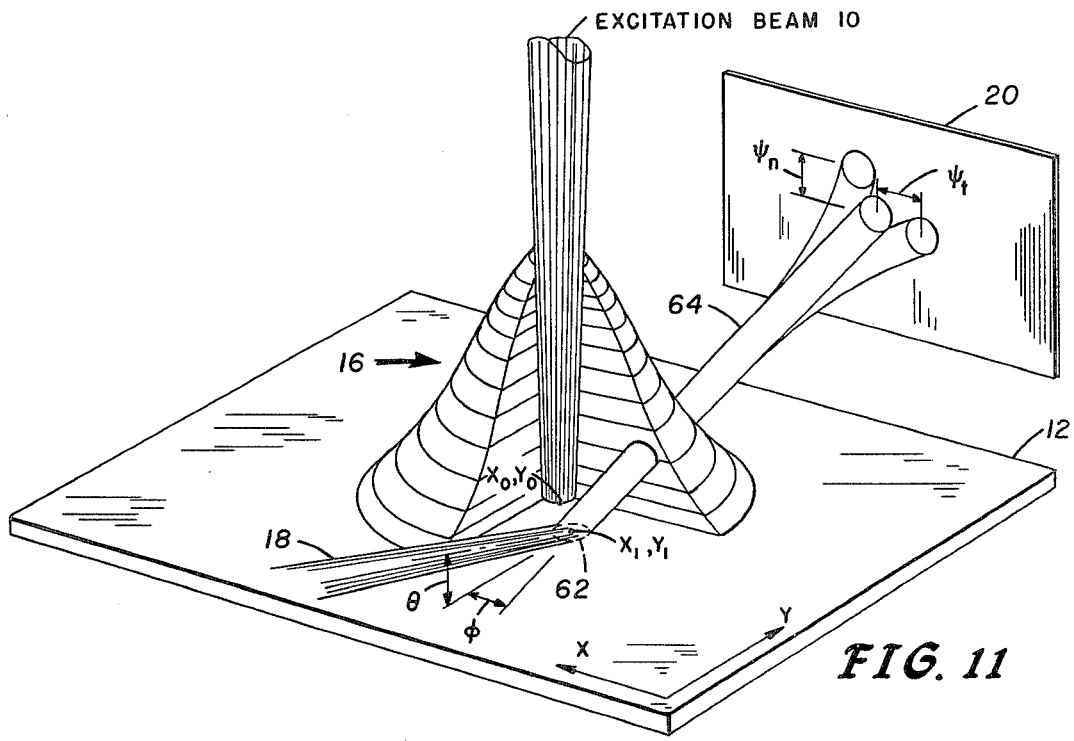
FIG. 11 is an enlarged diagrammatic representation of an alternative optical beam deflection technique within the scope of the present invention wherein the optical probe beam is reflected from the sample surface.

FIG. 11 illustrates an alternative scheme for scanning the thermal lens 16, wherein the optical probe beam 18 enters a thermal lens at an incident angle $(\theta,\phi)$, and is reflected from a point 62 on the sample surface 12. The reflected beam travels out through the thermal lens 16 and is refracted as it passes through the thermal lens. The vectorial deflection of the reflected beam 64 is measured and recorded by the optical detecting means 20. The characteristics of the optical probe beam 18, the excitation beam 10 and the fluid is the same as in the optical beam skimming mode illustrated in FIG. 1. The optical probe beam is made to scan the thermal lens 16 and deflection of the reflected beam 64 is measured for various incident angle parameters $(\theta,\phi)$ and for various reflection location coordinates $(X_1, Y_1)$. To generate the temperature profile of a large area, the excitation beam 10 can be pointed to a plurality of positions $(X_o, Y_o)$ and the optical probe beam 18 can scan each thermal lens 16. The scanning scheme for the reflected optical probe beam is similar to those used with the skimming optical probe beam and are illustrated in FIGS. 6, 7 and 8. The present mode has an advantage over the skimming optical beam mode (FIG. 1) in that the motion of the optical beam detector 20 is not a significant source of error, because this mode does not have deflection angle amplification with distance from the target as in the skimming mode. In the present mode, the apparent location of the reflected spot $(X_1, Y_1)$ will appear at a different location as the reflected beam 64 is refracted by the thermal lens 16.

Figure 12A:
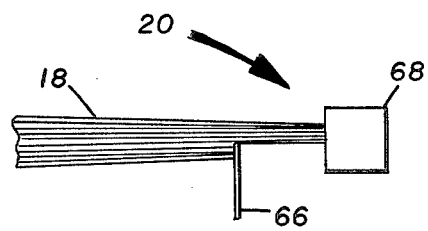
FIGS. 12a–b illustrate the use of a knife edge as the optical detecting means.
Figure 12B:
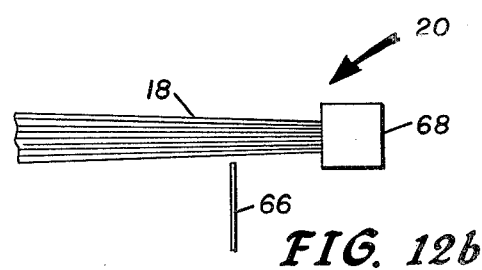

FIGS. 12a–b illustrate an alternate optical detecting means 20. The optical detecting means uses a knife edge 66 and a photodetector 68 which produces an output voltage which varies as some function of the light intensity. As the optical probe beam 18 is deflected more or less light will reach the photodetector 68 and its output voltage will increase or decrease respectively. By various orientations of the knife edge 66, the optical detecting means 20 can be used to determine either the normal or transverse deflection component. The signal generated by the photodetector 68 is processed by a similar approach to that shown in FIG. 4.

Figure 13:
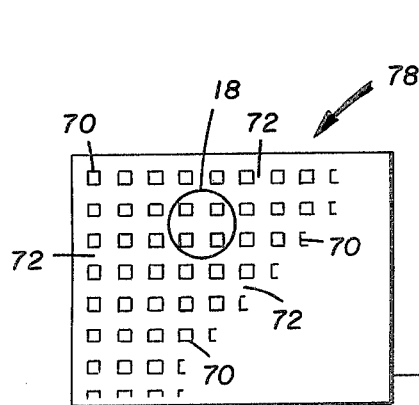
FIG. 13 is a block diagramatic representation of an alternative optical detecting means using an array of sensors.

FIG. 13 shows in block diagramatic form another optical detecting means 20, which utilizes an array detector. The array detector comprises: an array of optical resolution elements 70 separated by blank spaces 72; an amplifier and processor 74; and, a recorder 76. The resolution elements 70 are smaller in size than the optical probe beam 18 and the signal produced by each resolution element 70 is directly proportional to the area of that resolution element illuminated by the optical probe beam 18. The amplifier and processor 74 amplifies a signal generated by each resolution elements and processes the signal either by a series or parallel computation scheme and provides as output the coordinate position of the probe beam 18 on the surface of the array 78. Use of the detector array 78 to decode the positionally modulated optical probe beam 18 can be understood in terms of the knife edge detection method illustrated in FIGS. 12a–b. The physical edge of each detector element 70 acts as a knife edge aperture. The integrated intensity incident on the detector associated with a broadened optical probe beam are caused by the positional modulation of the optical probe beam as it passes through the dynamic thermal lens. As the intensity changes the voltage output from each detector element changes, in a corresponding manner, thus indicating the shape of the thermal lens 16.

Figure 14:
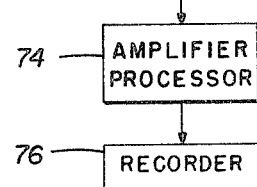
FIG. 14 illustrates a second method, within the scope of the present invention, of operating the array detector using principles of interferometry.
Figure 14:
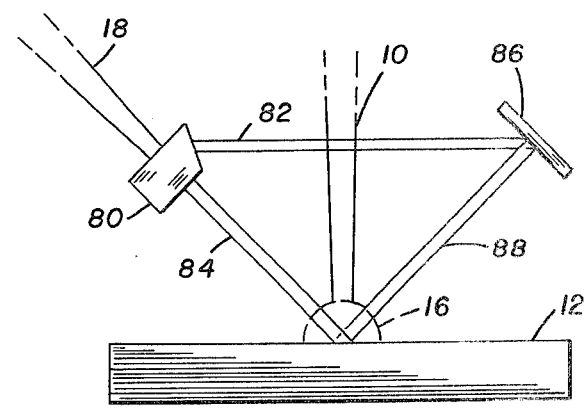

FIG. 14 illustrates a second method of operating the array detector which uses principles of interferometry. A beam splitter 80 is inserted in the optical probe beam 18 path and separates the optical beam into a reference beam 82 and a signal beam 84. The reference beam 84 is directed to the array detector 86. The signal beam 84 is reflected from the sample surface and directed through the thermal lens 16 to the array detector 86. If the probe beam 18 is coherent, i.e., a laser, then the reference beam 82, and the signal beam 84 which is deviated by the thermal lens, will interfere at the array detector 86. The degree of interference depends on the relative optical path lengths of the two beams (82, 86) and is a measure of the dynamic change to the signal beam 88 caused by the thermal lens 16. The output voltage of each element of the detector array 86 is a measure of the signal probe beam 88 path deflection associated with discrete points on the sample surface. By adjusting the reference beam phase front, the transverse and normal deflection components of the signal beam 88 can be individually displayed.

As discussed previously, optical beam detection thermal imaging is used to detect thermal blooming caused by areas of localized heating on the sample surface. The use of an excitation beam as a heating source to generate these areas of localized heating has been presented. However, it is within the contemplation of inventors to use optical beam deflection thermal imaging to detect localized hot spots on the sample surface generated by other means. Various mechanisms exist for generating such hot spots which are known to one skilled in materials testing. One such mechanism is the use of amplitude modulated ultrasound to generate an alternating stress relaxation process in the sample tested. Friction is generated in areas of small cracks or in partially bonded layers of a laminate structure. Such friction will cause localized heating and hot spots will form on the sample surface. These hot spots can be detected by the invented optical beam detection method.

The optical beam deflection method and apparatus can be used to detect the presence of inhomogenieties as described previously. It also has application in determining thermal conductivity of a homogeneous sample. The thermal lens 16 generated by the modulated excitation beam 10 will oscillate in shape at the same frequency as the excitation beam modulation frequency ($f_m$), but in a different phase relationship. This phase difference is a measure of how fast the thermal lens 16 is created, and provides a measure of the thermal conductivity or any other property which inhibits or accelerates the three-dimensional thermal flow. Also, as noted earlier, varying the frequency of modulation ($f_m$) for the exitation beam 10 allows one to select a particular layer of the sample surface for study. When the frequency of the excitation beam ($f_m$) is decreased, the thermal diffusion length is increased and the depth of analysis into the sample is increased. Conversely, when the modulation frequency ($f_m$) is increased the thermal diffusion length decreases and layers at or close to the surface are analyzed. In this manner, the thermal conductivity in a multi-layered wafer can be studied. When studying properties of a homogeneous sample the transverse and normal deflections of the probe beam, as well as the phase difference between the deflected signal and the excitation modulation ($f_m$), will be recorded.

While there has been described what is believed to be the preferred embodiments of the invention, and the preferred areas of application, those skilled in the art will recognize that other and further modifications may be made, and other applications are possible, without departing from the spirit of the invention, and it is intended to claim all such embodiments as fall within the scope of this invention.

What is claimed is:

1. An apparatus for the nondestructive testing of material, comprising:
    a narrow beam excitation means for generating a spatially localized area on the sample surface having a radial surface temperature gradient;
    a narrow optical probe beam directed through at least one of a plurality of positions, each position having a different transverse offset value ($\Delta$) measured from the point of intersection with said narrow beam excitation means, and passing through a thermal lens produced adjacent to said sample by said radial surface temperature gradient; and,
    an optical detecting means for measuring the transverse deflection ($\psi_t$) of said narrow optical probe beam for said at least one of a plurality of transverse offset valves ($\Delta$) thereby providing information as to the shape of said thermal lens which in turn indicates properties and features at the surface and subsurface layers of said sample.

2. The apparatus of claim 1 wherein said excitation beam means is modulated to produce a dynamic temperature change on said sample surface causing said thermal lens generated from said radial surface temperature gradient to alternate in size, and wherein said optical detecting means measures the amplitude and phase of the normal and transverse components of said optical probe beam deflection vector as function of time for said at least one of a plurality of transverse offset values ($\Delta$).

3. The apparatus of claim 2 wherein said optical detecting means measures normal and transverse components of said optical probe beam deflection vector at a particular modulation phase of said excitation beam.

4. The apparatus of claim 2 or 3 wherein the frequency of said excitation beam means modulation ($f_m$) is decreased to increase the thermal diffusion length into said sample and therefore to increase the depth of analysis into said sample.

5. The apparatus of claim 2 or 3 wherein the frequency of said excitation beam means modulation ($f_m$) is increased to decrease the thermal diffusion length into said sample and therefore decrease the depth of analysis into said sample.

6. The apparatus of claim 2 or 3 wherein the frequency of said excitation beam means modulation ($f_m$) varies from 1 Hz to 1 KHz.

7. The apparatus of claim 2 or 3 wherein said excitation beam means is amplitude modulated.

8. The apparatus of claim 2 or 3 wherein said excitation beam means is modulated in a pulsing manner.

9. The apparatus of claim 2 or 3 wherein said excitation beam means is modulated by spatially varying its position.

10. The apparatus of claim 1, 2 or 3 wherein said optical detecting means is a knife edge detector.

11. The apparatus of claim 1, 2 or 3 wherein said optical detecting means is an array of detectors comprising:
    an array of resolution elements, each of said resolution elements being separated by a blank zone and each being small in size compared to said optical probe beam; and,
    detection circuitry for processing signals from each of said resolution elements to determine the vectorial displacement of said optical probe beam.

12. The apparatus of claim 1, 2 or 3 wherein said optical probe beam skims said sample surface at a normal offset distance ($Z_o$) from said surface.

13. The apparatus at claim 12 wherein said optical probe beam scans in a transverse manner across said thermal lens and wherein said optical detecting means measures said optical probe beam vectorial deflection for discrete transverse displacement ($\Delta$) values.

14. The apparatus of claim 13 wherein said excitation beam means is pointed to a plurality of positions ($X_o$, $Y_o$) on said sample surface and wherein said optical probe beams transversely scans said thermal lens generated from each of said excitation beam means positions, and wherein said optical detecting means measures said optical probe beam vectorial deflection for each ($X_o$, $Y_o$, $\Delta$) input parameters.

15. The apparatus of claim 12 wherein said optical probe beam is held stationary and said excitation beam means is pointed to a plurality of ($X_o$, $Y_o$) positions on said sample surface generating said thermal lens which is intersected by said stationary optical probe beam, and wherein said optical detecting means measures said optical beam vectorial deflection for each ($X_o$, $Y_o$, $\Delta$) input parameter.

16. The apparatus of claim 12 wherein said optical probe beam intersects said excitation beam means, said transverse offset value ($\Delta$) equaling zero, and wherein said optical detecting means measures the transverse deflection ($\psi_t$) of said probe beam.

17. The apparatus of claim 16 wherein said excitation beam means is pointed to a plurality of positions ($X_o$, $Y_o$) on said sample surface and wherein said optical detecting means measures said transverse deflection ($\psi_t$) of said optical probe beam for each excitation beam means position ($X_o$, $Y_o$).

18. The apparatus of claim 1, 2 or 3 wherein said optical probe beam enters said thermal lens at an incident angle ($\theta,\phi$) and is reflected from a location ($X_1$, $Y_1$) on said sample surface, back out through said thermal lens, and wherein said optical detecting means measures said optical probe beam vectorial deflection for ($\theta,\phi$, $X_1$ $Y_1$) parameters.

19. The apparatus of claim 18 wherein said optical probe beam scans said thermal lens producing a plurality of different ($\theta,\phi$, $X_1$, $Y_1$) parameters and wherein said optical detecting means measures said optical probe beam vectorial deflection for each ($\theta,\phi$, $X_1$, $Y_1$) input parameter.

20. The apparatus of claim 19 wherein said excitation beam means is pointed to a plurality of positions ($X_o$, $Y_o$) on said sample surface, said optical probe beam scanning said thermal lens produced by each of said excitation beam positions, and wherein said optical detecting means measures said optical probe beam vectorial deflection for each ($\theta,\phi$, $X_1$, $Y_1$, $X_o$, $Y_o$) input parameter.

21. The apparatus of claim 1, 2 or 3 wherein said optical detecting means is a silicon wafer position detector having output voltage dependent on the location said optical probe beam strikes said wafer surface and wherein the time varying amplitude of the output voltage is recorded.

22. The apparatus of claim 21 wherein said silicon wafer position detector further comprises:
an amplifier connected to said silicon waver position detector;
an excitation beam modulator for modulating said excitation beam means;
an oscillator which provides a reference signal to control an excitation beam modulator;
a lock-in amplifier connected to said amplifier, synchronized by reference signals from said oscillator, to detect the deflection signal generated by said silicon wafer position detector at a particular phase of the excitation beam modulation cycle; and,
a recorder connected to said lock-in amplifier for recording deflection amplitude.

23. The apparatus of claim 21 wherein said silicon wafer position detector will record said amplitude of output voltage at the same modulation phase of said excitation beam means.

24. The apparatus of claim 2 in which said optical detecting means includes a detector array, and in which said apparatus further comprises a beam splitter to split said optical probe beam into a reference beam and a signal beam, said reference beam being directed to said detector array, said signal beam being directed through said thermal lens to said detector array such that an interference pattern between said reference beam and said signal beam is produced and detected by said detector array.

25. The apparatus of claim 1 wherein said thermal lens is generated in a fluid which is a gas.

26. The apparatus of claim 25 wherein said gas is at atmospheric pressure.

27. The apparatus of claim 25 wherein said gas is at below atmospheric pressure.

28. The apparatus of claim 1 wherein said excitation beam means is projected normal to said sample surface.

29. The apparatus of claim 1 wherein said excitation beam means is projected at an angle relative to said sample surface.

30. The apparatus of claim 1 wherein said excitation beam means is produced by a laser source producing a circular beam of light having a gaussian distribution.

31. The apparatus of claim 1 wherein said optical probe beam is coherent light.

32. The apparatus of claim 1 wherein said optical probe beam is incoherent light.

33. The apparatus of claim 1 wherein said optical probe beam is small in diameter compared to said thermal lens.

34. The apparatus of claim 1 wherein said excitation beam means is electromagnetic energy varying from the microwave frequency ($10^9$ Hz) to the ultraviolet light frequency ($10^{15}$ Hz).

35. The apparatus of claim 1 wherein said excitation beam means is a particle beam.

36. The apparatus of claim 1 wherein said optical probe beam is 1 mm in diameter.

37. The apparatus of claim 1 wherein said thermal lens is generated in a fluid which is a liquid.

38. A method of thermal imaging comprising the steps of:
applying energy to a sample to produce a spatially localized area on the sample surface having a radial surface temperature gradient, said radial surface temperature gradient produces in a fluid adjacent to said sample surface, a localized volume having an alternating refractive index;
directing an optical probe beam through at least one of a plurality of positions, each position having a different transverse offset value ($\Delta$) measured from the point of intersection with said narrow beam excitation means and passing through said volume of alternating refractive index which causes said optical probe bean to be deflected; and, measuring the transverse deflection ($\psi_t$) of said optical probe beam for said at least one of a plurality of transverse offset values ($\Delta$) to provide information on properties and features at the surface and subsurface layers of said sample.

39. A method of thermal imaging to detect localized thermal hot spots on a sample surface, comprising the steps of:

directing an optical probe beam through at least one of a plurality of positions, each position having a different transverse offset value ($\Delta$) measured from the center point of said hot spot and passing through a thermal lens produced by a radial surface temperature gradient in a fluid adjacent to said localized thermal hot spot; and, measuring the transverse deflection ($\psi_t$) of said optical probe beam caused by said thermal lens for said at least one of a plurality of transverse offset values ($\Delta$) to provide information on properties and features at the surface and subsurface layers of said sample.

40. A method of thermal imaging comprising the steps of:

directing an excitation beam to the surface of a sample for generating a spatially localized area on the sample surface having a radial surface temperature gradient;

directing an optical probe beam through at least one of a plurality of positions, each position having a different transverse offset value ($\Delta$) measured from the point of intersection with said narrow beam excitation means, and passing through a thermal lens produced adjacent to said sample by said radial surface temperature gradient; and, measuring the transvere deflection ($\psi_t$) of said optical probe beam for said at least one of a plurality of transverse offset values ($\Delta$) to provide information on properties and features at the surface and subsurface layers of said sample.

41. The method of claim 40 wherein said excitation beam is modulated and the normal and transverse deflection components of said optical probe beam are measured as well as the phase difference between said excitation beam and said optical probe beam's deflection.

42. The method of claim 41 wherein said optical probe beam is directed to skim the sample surface at an offset distance ($Z_o$) above the surface.

43. The method of claim 42 including the steps of:
scanning the optical probe beam in a transverse manner across said thermal lens; and
measuring the transverse deflection ($\psi_t$) of said optical probe beam for discrete transverse offset values ($\Delta$).

44. The method of claim 43 including the steps of:
directing the excitation beam to a plurality of positions on said sample surface;
scanning each of said thermal lens generated by each of said excitation beam positions.

45. The method of claim 44 wherein the optical probe beam is directed to intersect the excitation beam, said transverse offset value ($\Delta$) equaling zero; and wherein the transverse deflection ($\psi_t$) optical probe beam is measured.

46. The method of claim 40 wherein said optical probe beam is directed to enter said thermal lens at an incident angle and is reflected from a location on the sample surface; and, measuring the vectorial deflection of the reflected optical probe beam.

* * * * *